(12) United States Patent
Roth

(10) Patent No.: US 6,662,651 B1
(45) Date of Patent: Dec. 16, 2003

(54) PORTABLE EXERCISE DEVICE

(75) Inventor: Wilfred Roth, Burlington, VT (US)

(73) Assignee: Javelin Sports, Inc., Burlington, VT (US)

( * ) Notice: Subject to any disclaimer, the term of this patent is extended or adjusted under 35 U.S.C. 154(b) by 0 days.

(21) Appl. No.: 10/219,146

(22) Filed: Aug. 15, 2002

(51) Int. Cl.$^7$ ................................................. A61B 1/24
(52) U.S. Cl. ..................................................... 73/379.02
(58) Field of Search .................... 73/379.01, 379.02, 73/379.03, 379.08, 379.09, 788, 794, 862, 833, 856

(56) References Cited

U.S. PATENT DOCUMENTS

| | | | |
|---|---|---|---|
| 3,672,219 A | 6/1972 | Van Patten | 73/379 |
| 3,677,543 A | 7/1972 | Richardson | 272/82 |
| 3,893,276 A * | 7/1975 | Brown | 52/475.1 |
| 3,949,517 A | 4/1976 | Reiner et al. | 46/45 |
| 4,019,734 A | 4/1977 | Lee et al. | 272/137 |
| 4,216,467 A * | 8/1980 | Colston | 341/20 |
| 4,613,130 A | 9/1986 | Watson | 272/135 |
| 4,647,038 A | 3/1987 | Noffsinger | 272/123 |
| 4,733,862 A | 3/1988 | Miller | 272/137 |
| 4,762,318 A | 8/1988 | Phillips et al. | 272/137 |
| 4,909,505 A | 3/1990 | Tee | 272/136 |
| 5,063,788 A * | 11/1991 | Ch'Hayder et al. | 73/862.043 |
| 5,152,183 A * | 10/1992 | Munzebrock | 73/862.56 |
| D342,688 S | 12/1993 | Jackson | D10/85 |
| 5,317,916 A | 6/1994 | Kovacevic | 73/379.03 |
| 5,505,677 A | 4/1996 | Hinds | 482/10 |
| 5,538,486 A | 7/1996 | France et al. | 482/8 |
| 5,629,972 A * | 5/1997 | Hausmann et al. | 378/170 |
| 5,723,785 A | 3/1998 | Manning | 73/379.03 |
| 5,871,424 A | 2/1999 | Conner | 482/129 |
| 5,909,939 A * | 6/1999 | Fugmann | 33/503 |
| 5,959,200 A * | 9/1999 | Chui et al. | 73/105 |
| 6,010,430 A | 1/2000 | Mankovtiz | 482/8 |
| 6,015,357 A * | 1/2000 | Rizza | 473/583 |
| 6,093,136 A | 7/2000 | Whipple | 482/123 |
| 6,149,550 A | 11/2000 | Shteingold | 482/8 |
| 6,322,483 B1 | 11/2001 | Rotella | 482/129 |

* cited by examiner

*Primary Examiner*—Max Noori
(74) *Attorney, Agent, or Firm*—Downs Rachlin Martin PLLC

(57) ABSTRACT

A portable exercise device (20) having a force measuring system (28) and a length adjuster (30). The exercise device includes a pulley/securing device assembly (22) and a cord (24) having a gripping structure (26) at each of its ends. The pulley/securing device assembly has a pulley (38) for engaging the cord and a securing device (34) for securing the exercise device to a door (46). The force measuring system engages one of the gripping structures and determines magnitude of a tensile force (68) applied to that gripping member. The force measuring system is in communication with an electronic display (88') that displays the magnitude of the tensile force to a user (27). The force measuring system may be powered by batteries (104, 104') contained in the housing of the force measuring system, contained in a handgrip (52) of the gripping structure, or located aboard the electrified glove, may be powered by a power generating system (132) driven by the pulley during, or may be powered by a piezoelectric sensor (72) used to measure the force applied to the cord. The length adjuster includes a body (162) having a plurality of slots (164) that threadedly receive a portion of the cord and allow a user to create, and adjust the size of, an excess loop (190) to change the effective length of the cord.

3 Claims, 9 Drawing Sheets

PORTABLE EXERCISE DEVICE

FIELD OF THE INVENTION

The present invention relates generally to the field of exercise equipment. More particularly, the present invention is directed to a portable exercise device.

BACKGROUND OF THE INVENTION

Portable exercise devices of various sorts are known. One type of exercise device that has received some measure of success in the marketplace over the years is a cord-and-pulley device that may be removably attached to a door, e.g., the door of a hotel room, office, or house, among others, that provides a temporary support for the device while it is in use. This type of exercise device is useful for, among other things, aerobic exercise, resistance training, and rehabilitative therapy, such as strength and range-of-motion therapy. These exercise devices are typically lightweight and compact, two key criteria for portability, which is often an important selling point for the devices. Another important feature of this type of exercise device is that it is easily used in virtually any setting having a relatively sturdy door that can support the device during use.

An example of such an exercise device is the Travel Trainer™ device available from Javelin Sports, Inc., Burlington, Vt. The Travel Trainer™ device includes a fixed length of rope, or cord, and a pulley attached to a securing device, which is removably mountable to a door or similar structure. The cord has a loop formed adjacent each of its ends that engages a corresponding handgrip that a user may grip with one of his/her hands, or other body part, while using the exercise device. Each loop is formed by securing an end portion of the cord to another portion of the cord with a compression sleeve crimped into firm engagement with these two portions of the cord. The cord engages the pulley, which allows a user to move the handgrips in a reciprocating fashion with substantially negligible wear on the cord while applying generally counterbalancing forces to the handgrips. In this manner, the user can exercise various body parts by reciprocatingly moving the handgrips repeatedly for a period of time while maintaining a suitable amount of tension in the cord. The user may change the resistance by changing the angle the his/her body forms with respect to vertical. For example, when the user's body performs a particular exercise with his/her body at a 45° angle with respect to vertical, the resistance will be greater than when the user's body performs the same exercise with his/her body at a 20° angle with respect to vertical.

A drawback of conventional exercise devices such as the Travel Trainer™ device is that the fixed length of cord provided with the device does not provide any adjustability of the device to suit various conditions, such as the height of the user, the height of the door the user mounts the device to, and/or the type of exercise the use desires to perform. Another drawback of these conventional exercise devices is that they generally do not include any means for permitting a user to determine how much force he/she is applying to the cord during a workout. The present invention overcomes these and other shortcomings of conventional exercise devices.

SUMMARY OF THE INVENTION

In one aspect, the present invention is directed to a system for measuring a force. The system comprises a generally triangular-shaped force-carrying element that includes a first leg and a second leg that generally converge with one another to form a crotch having a center. Each of the first and second legs have a distal end spaced from the crotch. A third leg extends between the distal ends of the first and second leg to keep the distal ends spaced from one another. A sensor is operatively coupled to the first and second legs between the crotch and the third leg for sensing a change in distance between the first and second legs when a force is applied to the third leg generally along a line extending through the center of the crotch.

In another aspect, the present invention is directed to a length adjuster for an elongate flexible member having a length, a transverse dimension, a first portion, and a second portion spaced from the first portion along the length of the elongate flexible member, wherein the elongate flexible member carries a tensile force therein. The length adjuster comprises a body having a longitudinal axis, a first end, and a second end spaced from the first end along the longitudinal axis. A plurality of slots is formed in the body for receiving the elongate flexible member therein in a serpentine manner. Each of the plurality of slots has a width substantially equal to or less than the transverse dimension of the elongate flexible member. At least some of the plurality of slots are oriented substantially transverse to the longitudinal axis so as to form a plurality of outside corners. At least some of the outside corners interact with the elongate flexible member when the elongate flexible member is engaged with the plurality of slots so as to transfer at least a portion of the tensile force from the elongate flexible member into the body. A first one of the plurality of slots is located adjacent the first end of the body and configured so that the first portion of the elongate flexible member extends away from the first end when the elongate flexible member is engaged in the plurality of slots and is carrying the tensile force. A second one of the plurality of slots is located adjacent the second end of the body and configured so that the second portion of the elongate flexible member extends away from the second end when the elongate flexible member is engaged in the plurality of slots and is carrying the tensile force.

In a further aspect, the present invention is directed to an exercise device comprising a pulley having a rotational axis. An elongate flexible member engages the pulley in a manner that causes the pulley to rotate about the rotational axis when the elongate flexible member is moved relative to the pulley. The exercise device further comprises an electronic display and a generator operatively coupled to the pulley and to the electronic display so that the pulley drives the generator and the generator provides power to the electronic display when the elongate flexible member causes the pulley to rotate.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE DRAWINGS

Figure 1:
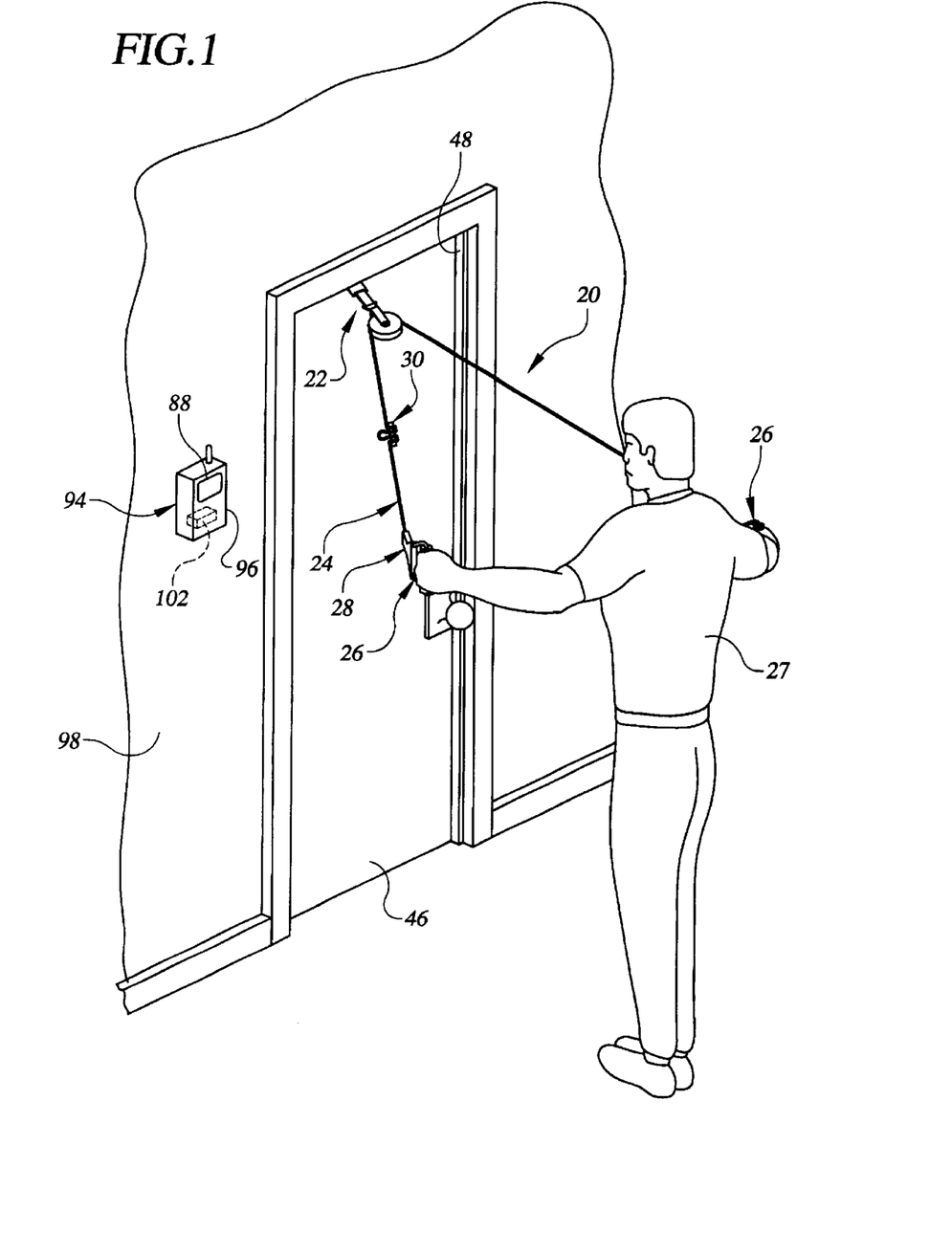
FIG. 1 is a perspective view of a user using an exercise device of the present invention.
Figure 2:
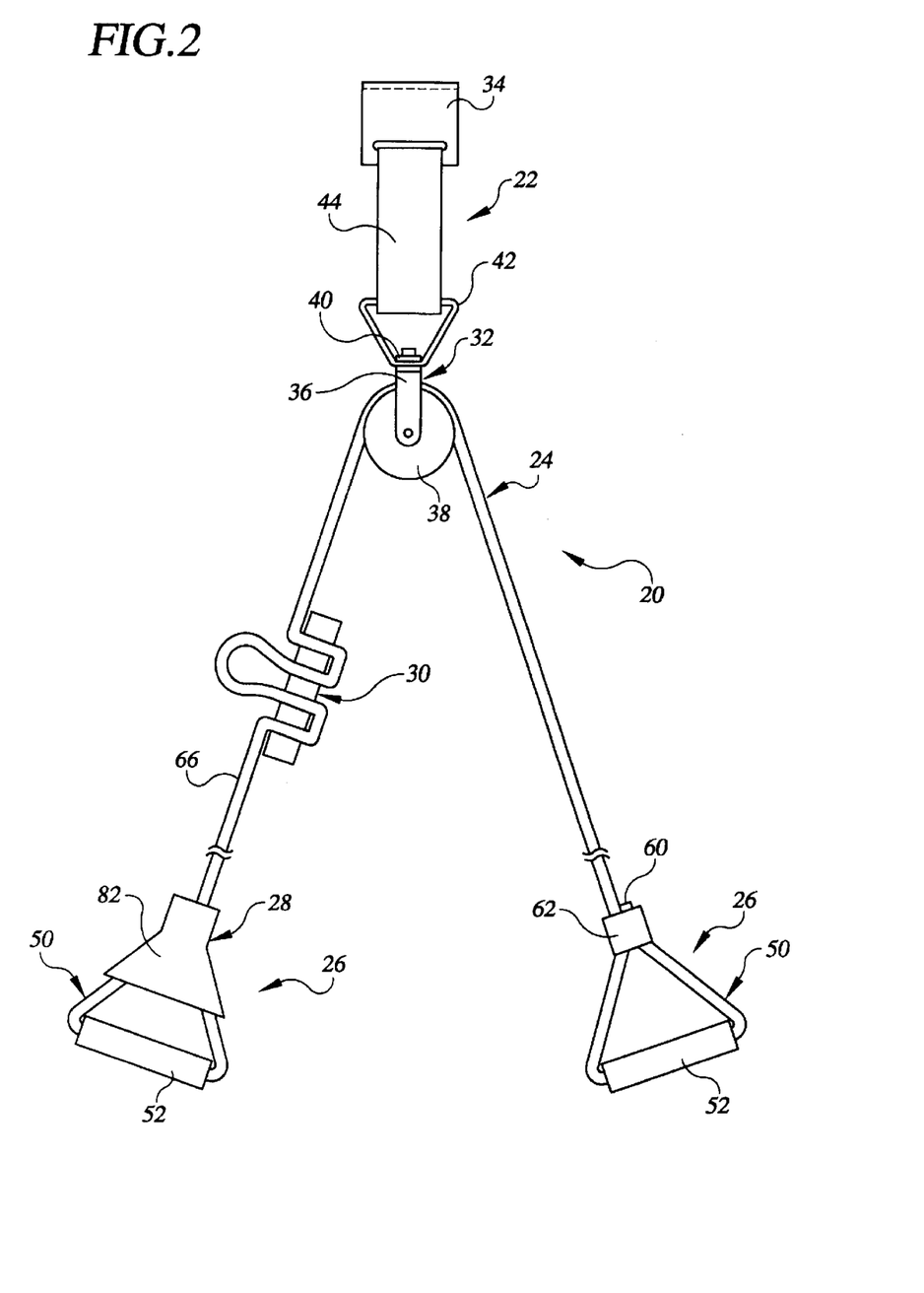
FIG. 2 is an enlarged top view of the exercise device shown in FIG. 1.

Referring now to the drawings, wherein like numerals indicate like elements, FIGS. 1 and 2 show in accordance with the present invention an exercise device, which is generally denoted by the numeral 20. Generally, exercise device 20 is a reciprocating action, pulley-type device comprising a pulley/securing device assembly 22 and a cord 24 having a gripping structure 26 located at each of its ends. Those skilled in the art will appreciate that a user 27 may use exercise device 20 in any of a number of ways that allows the user to exercise many major muscle groups of his/her body. Accordingly, although gripping structures 26 are so called because they most commonly provide places for user 27 to grip exercise device 20 with his/her hand, the user may also engage his/her feet and/or other body parts with the gripping structures, if desired.

Exercise device 20 includes a number of features, such as a force measuring system 28 and a length adjuster 30 for cord 24, that make the exercise device more desirable to a user than similar conventional exercise devices, which do not include the present inventive features. Force measuring system 28, length adjuster 30, and other features of the present invention are described below in detail. Although these features are shown and described in the context of the reciprocating-action, pulley-type exercise device 20 illustrated, those skilled in the art will appreciate that the various features of the present invention may be used individually or in various combinations with one another with other types of exercise devices (not shown), e.g., cable- or cord-type devices utilizing weights or other resistance means, or devices other than exercise devices where it is desirable to adjust the length of a cord, or other elongate flexible member and/or determine the force applied to a body, such as a cord.

Pulley/securing device assembly 22 may include a block 24 and pulley subassembly 32 and a securing device 34. Block and pulley subassembly 32 allows cord 24 to change direction while allowing user 27 to move gripping structures 26 in a reciprocating manner with substantially negligible wear on the cord while applying generally counterbalancing forces to the gripping structures. Block and pulley subassembly 32 generally includes a block 36 and a pulley 38 rotatably mounted to the block. Block 36 and pulley 36 may be made of any suitable materials, such as metal or plastic, among others. Block 36 may include, among other things, a pivot connector 40 that allows pulley to pivot about a longitudinal axis of the block so that user 27 may use exercise device 20 with cord 24 in any plane necessary to perform a particular exercise. Block 36 may also include loop connector 42 for receiving a strap 44, or other member, for attaching the block to securing device 36. Strap 44 may be made of any suitable material, such as nylon webbing, among many others. Those skilled in the art will readily understand the variety of ways pulley 38 may be connected to securing device 36 such that the present example is sufficient to enable a skilled artisan to practice the present invention with any of a number of suitable alternatives.

Securing device 36 may be configured for securing exercise device 20 to a stationary object, such as a door 46. For example, securing device 36 may be configured to be hooked over the top of a swing-type door and captured in the space between the door and upper portion of a doorjamb 48, as shown in FIG. 1. Of course, securing device 36 may be of another type for securing exercise device 20 to objects other than doors. Those skilled in the art will be familiar with the various securing devices that may be provided such that an exhaustive recitation need not be presented herein.

Figure 3A:
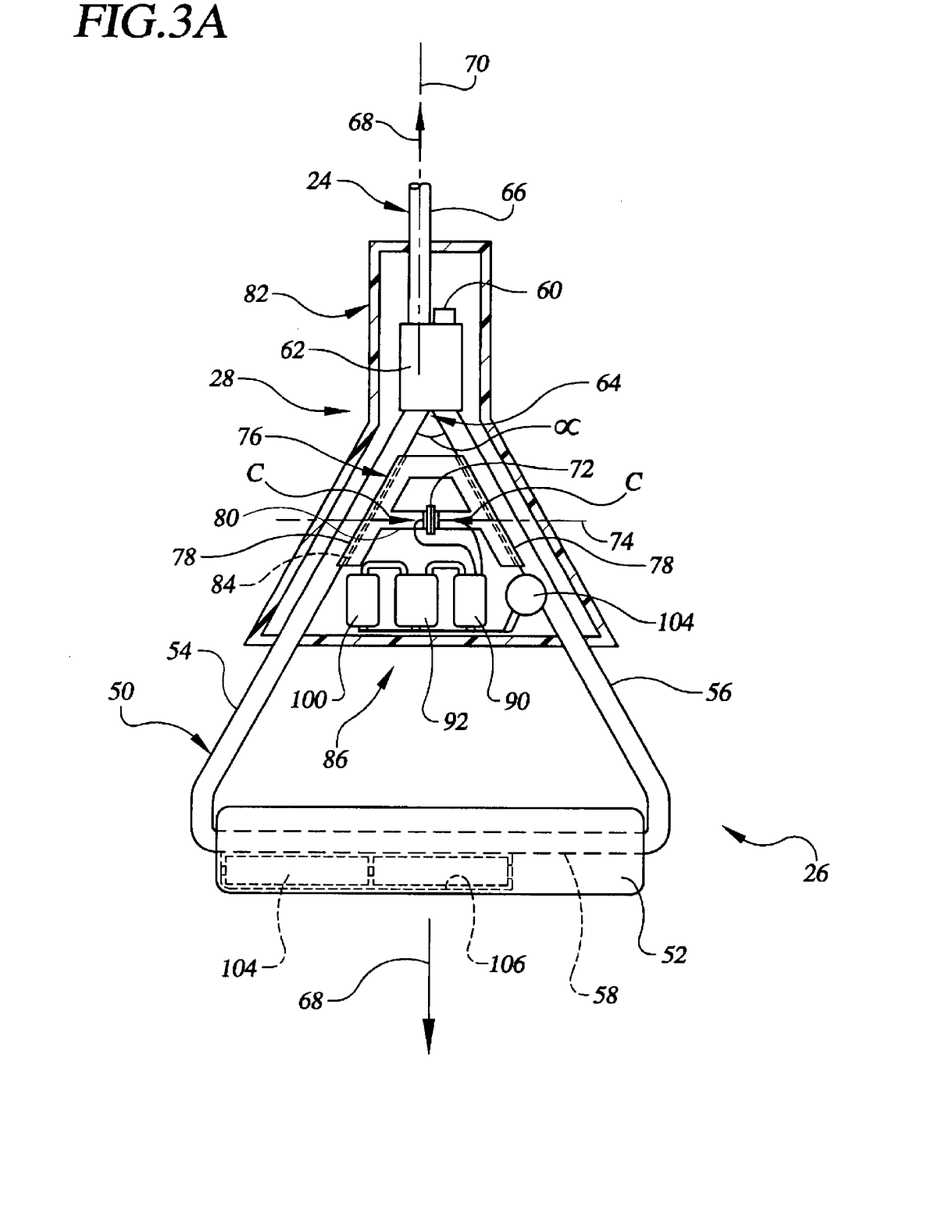
FIG. 3A is a partial cutaway view and simplified schematic diagram of the force measuring unit of the exercise device of FIGS. 1 and 2 showing the gripping structure.

Referring now to FIGS. 2 and 3A, each gripping structure 26 may include a loop 50 made from cord 24 and a handgrip 52 positioned within the loop so that the gripping structure generally forms a triangle having two legs 54, 56 comprising two portions of the loop of the cord and one leg 58 comprising the handgrip and a portion of the loop that extends through the handgrip. Legs 54, 56 are preferably, but not necessarily, of equal length. Each loop 50 may be formed in any suitable manner, such as capturing the free end 60 and another portion of cord 24 in a compression sleeve 62 and securing these parts to one another by crimping the compression sleeve. Depending upon the type of cord 24 used, other means for securing each free end 60 to a corresponding portion of the cord include melt-bonding, lashing, weaving, clamping, and adhesive bonding, among others. Alternatively, each loop 50 may be eliminated and replaced by a generally triangular gripping structure that is formed separately from cord and attached to cord in any suitable manner. Examples of such alternative gripping structure configurations are shown in U.S. Pat. No. 4,909,505 to Tee and U.S. Pat. No. 4,762,318 to Phillips et al., which are each incorporated by reference herein.

The generally triangular shape of gripping structure 50 generally forms a crotch 64 between legs 54, 56 that is opposite handgrip 52 and proximate a central portion 66 of cord 24. In the embodiment shown, wherein loop 50 of cord 24 actually forms a triangle, crotch 64 is formed at one of the vertices of the triangle. However, in other embodiments having alternative gripping structures, e.g., the gripping structure shown in U.S. Pat. No. 4,762,318 mentioned above, crotch 64 may not be formed at a vertex, but rather, e.g., at a region where legs 54, 56 diverge from one another but are separated at the crotch by another member. Preferably, but not necessarily, cord 24 is unlike rubber, i.e., is as non-stretchable and linearly elastic as practicable in the range of forces it will be subject to during normal use in the context of exercise device 20. For example, a suitable cord 20 is a "static," i.e., substantially non-stretchable, mountaineering rope. Generally, a cord is considered "static" when its elongation no greater than 1% under load. In contradistinction, a cord is considered "dynamic" if the elongation is 6% or more under load. Similarly, handgrip 52 is preferably, but not necessarily, as non-compressible and linearly elastic as possible. Example base materials for handgrip 52 include relatively hard plastics, wood, and metal, among others, which may or may not be covered with a softer outer covering comprising, e.g., rubber, foam, fabric, and/or gel, among other things.

If cord 24 is a dynamic cord, force measuring system 28 may measure the change in angle at formed between legs 54, 56 of the generally triangular gripping structure 26 as user 27 (FIG. 1) applies a force 68 to handgrip 52 in a direction substantially parallel with the longitudinal axis 70 of central portion 66 of cord 24. In the context of exercise device 20, force 68 will generally be applied to gripping structure 26 in a direction away from crotch 64 and will be counteracted by a generally equal force applied to the other gripping structure. Since such a force induces tension into legs 54, 56 of gripping structures 26 and central portion 66 of cord 24, force 68 is referred to herein as a tensile force. Those skilled in the art will appreciate that in other devices wherein cord 24 is replaced by another structure that can carry a longitudinal compressive force without buckling, the force may be also be applied in a direction toward crotch 64, thus producing a compressive force in legs 64, 66 of triangular gripping structure 26.

As tensile force 68 is applied to handgrip 52, legs 54, 56 elongate due to the tensile strain in loop 50 of cord 24, and angle a between these two legs decreases. In addition, handgrip 52 is generally placed into slight bending, which causes a further reduction in angle a between legs 54, 56. However, since handgrip 52 will typically be relatively stiff compared to the axial stiffness of cord 24 in loop 50, the contribution of decrease in angle a attributable to the bending of the handgrip will be relatively small. This decrease in angle a can be sensed in any of a number of manners, including by sensing a change in distance between legs 54, 56.

For example, force measuring system 28 may include a sensor 72, e.g., a piezoelectric sensor, that responds to a change in distance between legs 54, 56 along a line 74 that is substantially parallel to leg 58 of gripping structure 50. This change in distance may be measured directly using a strain sensor, e.g., a piezoelectric sensor, capacitive sensor, or resistive strain gage, among others, or indirectly, e.g., by measuring rate of change, using another type of sensor, such as a magnetic sensor. Those skilled in the art will appreciate the many types of sensors that may be used to implement force measuring system 28 of the present invention. Therefore, a detailed explanation of all possible sensors and configurations of force measuring system 28 is not necessary for those skilled in the art to practice the present invention.

Piezoelectric sensor 72 may be suitably mounted in a spreader 76 that supports the sensor and transmits a compressive force C to the sensor as tensile force 68 is applied to handgrip 52 and, correspondingly, to legs 54, 56 of gripping structure 26. Piezoelectric sensor 72 may be any size or shape desired and may be made of any suitable piezoelectric material. For example, piezoelectric sensor 72 may be disc-shaped and made of a lead-zirconate-titanate (PZT) ceramic. As those skilled in the art will understand, a PZT piezoelectric sensor generates a voltage thereacross that varies linearly with the strain induced into the piezoelectric sensor, at least within a certain range of strains.

Spreader 76 may be any suitable shape desired, and positioned at any suitable location between crotch 64 and handgrip 52. For example, spreader 76 may be the generally A-shaped frame shown and may be positioned proximate crotch 64. Spreader 76 may include two supports 78 each extending along a corresponding leg 54, 56 of gripping structure 26, and have attached thereto a cross member 80 for supporting therein generally in a sandwich configuration piezoelectric sensor 72, or other sensor. Entire spreader 76 may be made as an integral unit or, alternatively, may be made of two or more components that are subsequently joined to one another in any suitable manner known in the art. Spreader 76 may be made of any suitable material, such as a relatively rigid plastic, wood, or other dielectric material. If piezoelectric sensor 72 is insulated from spreader 76, or if supports 78 of the spreader are insulated from one another, spreader 76 may be made of a conductive material, such as metal. Piezoelectric sensor 72 may be secured in cross member 80 in any suitable manner, such as epoxy bonding, among others.

Force measuring system 28 may include a housing 82 to enclose and/or provide support for spreader 76. Housing 82 may be made of any suitable material, such as plastic. Spreader 76 may be attached to housing 82 to restrain the spreader from moving in concert with legs 54, 56 of gripping structure 26 as they elongate upon application of tensile force 68. Accordingly, each support 78 of spreader 76 may include a concave, relatively smooth surface 84 that cradles and allows legs 54, 56 of gripping structure 26 to slide therealong relatively easily. In an alternative embodiment, spreader 76 may be secured to one or both legs 54, 56 of gripping structure 26, e.g., at supports 78.

Those skilled in the art will readily appreciate that the triangular gripping structure 26 shown in FIG. 3A may be inefficient for certain sensors when cord 24 is static, i.e., relatively non-stretchable. This may be so since cord 24 will elongate only a small amount such that the change in the angle α and corresponding strain induced into cross-member 80 and piezoelectric sensor 72 will be too small for effectively measuring tensile force 68. To improve the performance of force measuring system 28 when cord 24 is relatively non-stretchable, spreader 76 may be designed to either spread legs 54, 56 apart from one another, or draw them toward one another, so that tensile force 68 induces a force into the spreader as a result of the change in direction of the legs caused by the spreader.

Figure 3B:
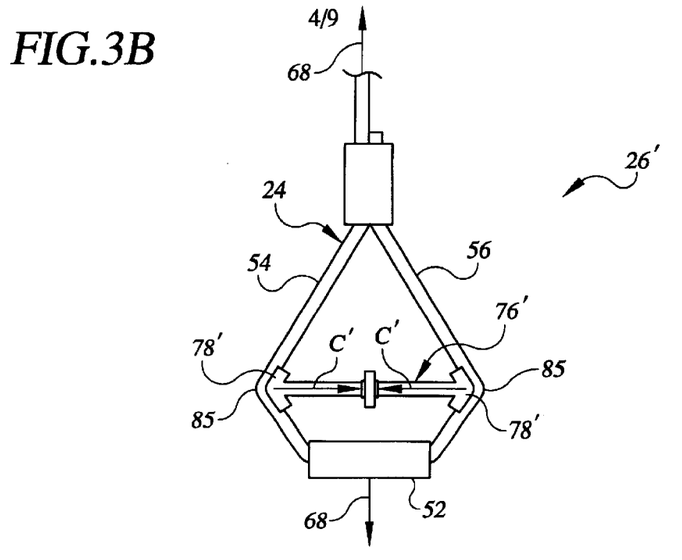
FIGS. 3B and 3C are each reduced-size views of alternative embodiments of the gripping structure shown in FIG. 3A.
Figure 3C:
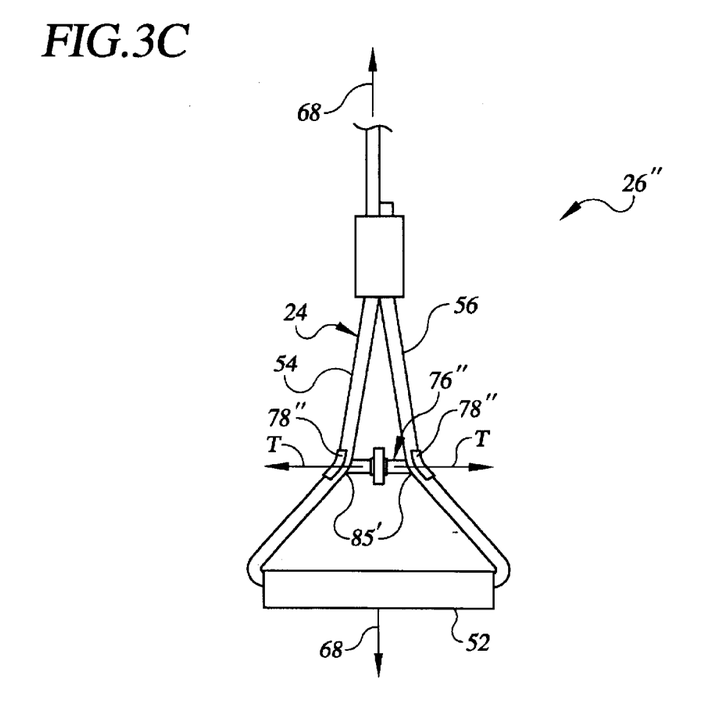

FIGS. 3B and 3C show, respectively, a gripping structure 26' having a spreader 76' that is sized to spread legs 54, 56 away from one another to form bends 85 and a gripping structure 26" having a spreader 76" that is sized to draw these legs toward one another to form bends 85'. Gripping structures 26', 26" may be considered generally triangular in that, but for the presence of the corresponding spreader 76', 76", these gripping structures would be substantially triangular in shape. Those skilled in the art will readily appreciate that providing bends 85, 85' in legs 54, 56 will cause tensile force 68 to induce either a compressive force C' or tensile force T into the corresponding spreader 76', 76". This is necessarily so because cord 24 is transversely flexible so that tensile force 68 would straighten out bends 85, 85' in the absence of spreaders 76', 76". However, spreaders 76', 76" counteract this straightening, resulting tensile force 68 inducing either counteracting compressive force C' or tensile force T into the spreader, as the case may be. Those skilled in the art will also readily understand how to calculate the magnitudes of compressive force C' and tensile force T given a particular configuration of a gripping structure/ spreader assembly and the magnitude of tensile force 68 applied to handgrip 52 such that a detailed presentation of the mathematics involved in calculating force C' or T is not necessary.

Like spreader 76 of FIG. 3A, spreaders 76' and 76" of FIGS. 3B and 3C, respectively, may be secured in place by attaching them to a housing (not shown, but which may similar to housing 82 of FIG. 3A), if provided, and/or one or both of legs 54, 56. Accordingly spreaders 76' and 76" may include supports 78',78" for engaging legs 54, 56 to create, respectively, bends 85, 85'. Supports 78', 78" may engage cord 24 in a suitable manner, such as the cradled engagement shown or a fully-enveloped engagement or a clamped engagement, among others. Those skilled in the art will appreciate that cord 24, being laterally flexible, cannot carry any significant compressive force without buckling. However, in a device where it is desired that force-measuring system 28 (FIGS. 1–3) be capable of measuring a compressive force rather than tensile force 68, each leg 54, 56 may be replaced by a pair of compression struts (not shown) connected to one another to effectively, if not actually, form a pinned joint at the location of bends 55, 55' in FIGS. 3B and 3C, respectively. The corresponding spreader may then be connected to, and span between, the pinned joints to maintain the joints in their generally spaced relation during loading.

Piezoelectric sensor 72 may be in electrical communication with circuitry 86 that utilizes a raw sensor signal, in the present case a varying voltage, as input, and that outputs a corresponding signal that causes an electronic display 88 (FIG. 1) to display the magnitude of tensile force 68 being applied to handgrips 52 by user 27. Circuitry 86 may include an analog-to-digital (A/D) converter 90 and a logic device 92, e.g., an application specific integrated circuit (ASIC). A/D converter 90 converts the analog voltage of the raw sensor signal into a digital signal suitable for use in logic device 92. Logic device 92 may implement one or more algorithms for calculating or otherwise determining the magnitude of tensile force 68 as a function of the digital signal. Tensile force 68 may be represented by an applied force signal that is output by logic device 92. For example, an algorithm may yield a value for the applied force signal by solving an equation having the digital signal from A/D converter 90 as an input variable or by looking up a value for the applied force signal based upon the digital signal. Those skilled in the art will understand the various algorithms that may be implemented in logic device 92 for determining applied force signal based upon the raw signal from piezoelectric sensor 72. Those skilled in the art will also appreciate that the algorithm(s) may be different depending upon the type of sensor used, e.g., magnetic or capacitive, among others, and the physical attribute sensed by that sensor. Optionally, the functionality of digital-type circuitry 86 shown may be implemented using only analog-type circuitry.

In the embodiment shown in FIG. 1, electronic display 88 is located remotely with respect to force measuring system 28. Accordingly, electronic display 88 may be generally contained within a monitor 94 having a housing 96, which may contain circuitry for displaying the magnitude of tensile force 64 to user and/or providing exercise device 20 with other functionality. Monitor 94 may be configured to be mounted to a wall 98, door 46, or other structure proximate the area in which user utilizes exercise device 20. Although electronic display 88 is shown as being integrated into a monitor 94 separate from force measuring system 28, it is noted that the display may be integrated within, or attached to, housing 82 of the force measuring system.

When electronic display 88 is located remote from force measuring system 28, the force measuring system may provide the applied force signal to the electronic display using a transmitter 100 and a corresponding receiver 102 located, respectively, within housing 82 of the force measuring system and housing 96 of monitor 94. Transmitter 100 and receiver 102 may be analog or digital and may operate using any suitable energy, such as radio frequency or infrared, among others. Alternatively, transmitter 100 and receiver 102 may each be replaced by a corresponding transceiver (not shown) to provide two-way communication between force measuring system 28 and monitor 94. Two-way communication may be desirable, e.g., when force measuring system 28 is augmented with other features (not shown), such as a force storage and recall feature or repetition counter, among others, that may be have controls incorporated into monitor 94. Transmitter 100 and receiver 102, or the alternative transceivers, need not be described in detail, since those skilled in the art will be familiar with these devices and how they may be implemented in connection with the present invention. In lieu of transmitter 100 and receiver 102, or pair of transceivers, monitor 94 may be hardwired to force measuring system 28 with suitable wires or cables (not shown) that provide either one-way or two-way communication, as the case may be.

Force measuring system 28 and monitor 94, of course, require electrical power in order to function. In addition, sensors other than piezoelectric sensor 72 may also require electrical power to function. This power may be provided by any one or more of various type of conventional storage batteries 104, e.g., nickel-cadmium, lead-acid, metal hydride, lithium ion, alkaline, and silver oxide zinc, among others. One or more batteries 104 for force measuring system may be contained, e.g., within housing 82 of force measuring system, and/or in a battery compartment 106 within handgrip 52. If one or more batteries 104 are provided in handgrip 52, wires (not shown) for placing the batteries in electrical communication with circuitry 86 of force measuring system 28 may be secured to, or embedded within, one or both legs 54, 56 of gripping structure 26. Similarly, one or more batteries (not shown) may be contained within housing 96 of monitor 94.

Figure 4:
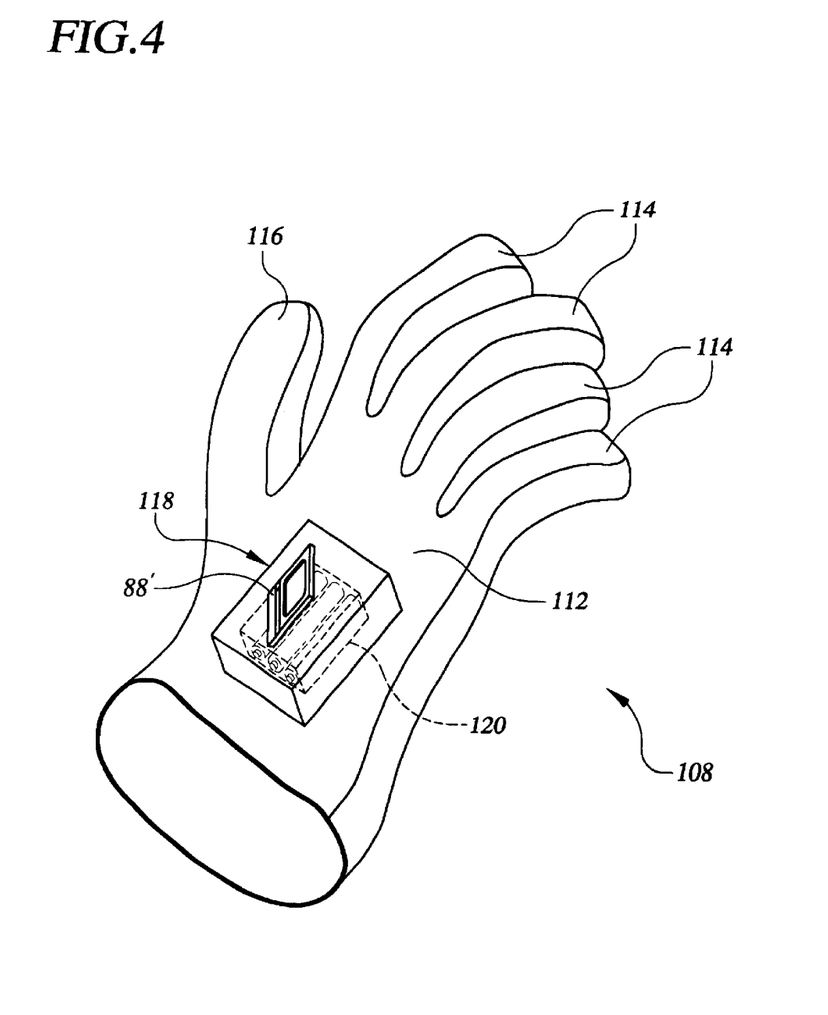
FIG. 4 is a perspective view showing the dorsal side of an electrified glove for powering various electronic devices that may be part of an exercise device of the present invention.
Figure 5:
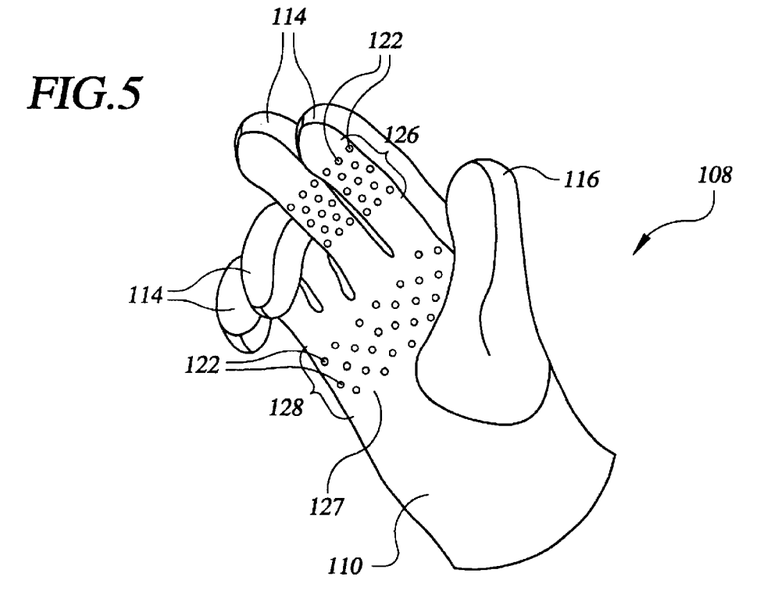
FIG. 5 is a perspective view of the volar side of the electrified glove of FIG. 8.
Figure 6:
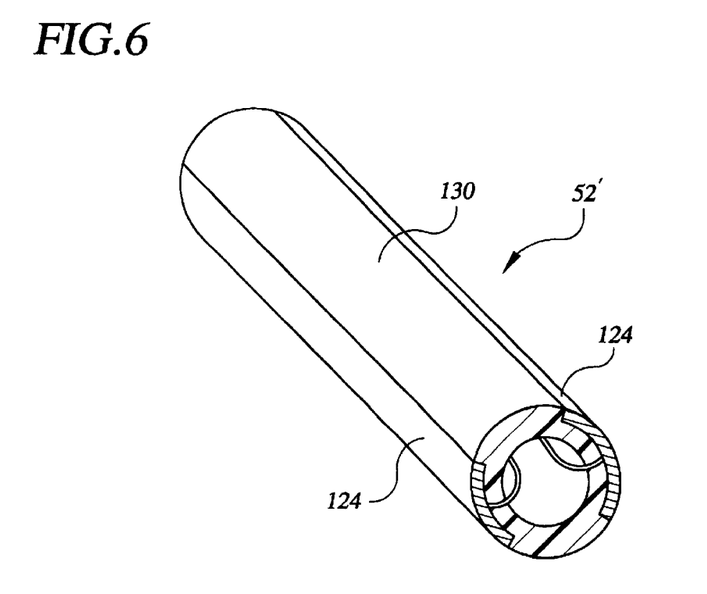
FIG. 6 is a cross-sectional perspective view of a handgrip of an exercise device of the present invention that may be used with the electrified glove of FIGS. 4 and 5.

Referring to FIGS. 4–6, in an alternative embodiment electrical power may be provided to force measuring system 28, monitor 94, and/or electronic display 88 from a battery 104' aboard a glove 108 that is electrified and worn by user 27 (FIG. 1) during use of exercise device 27. Glove 108 may be made in a manner that is the same as or similar to conventional gloves and, accordingly, may be made of any suitable material, such as natural or synthetic fabric, leather, polymer or other sheet, molded, or other type of material, or combination thereof. In general, glove includes a palm, or volar, side 110 and a dorsal side 112 spaced from the volar side. Glove 108 also generally includes four fingers 114, each of which may be full, i.e., covers the entire length of the corresponding finger of user 27, or partial, i.e., covers only a portion of the length of that finger. Glove 108 may optionally include a thumb 116 that may also be either full or partial.

Glove 108 may be electrified, e.g., by a battery pack 118 secured to the glove or located remote from the glove and in electrical communication therewith via wires (not shown) or other electrical conductors. In the latter case, battery pack 118 may be attachable to user 27 or clothing of the user, e.g., using a clip (not shown) or other securing device. Battery pack 118 may include a battery compartment 120 containing one or more batteries 104'. Battery pack 118 may be secured to glove 108, e.g., on dorsal side 112 thereof, using rivets (not shown) or any other suitable fastening means. To communicate electrical power from the one or more batteries 104' to force measuring system 28, monitor 94, and/or electronic display 88, volar side 110 of glove may include a plurality of electrical contacts 122 for contacting corresponding electrical contacts 124 on handgrip 52. Contacts 122 of glove 108 may be made of any conductive material, such as metal, and may be provided in any suitable number, size, shape, and/or location.

For example, contacts 122 may be provided in two groups, e.g., one group 126 for the positive side of the resulting circuit and one group 128 for the negative side, of generally circular contacts each having a convex contact surface for contacting electrical contacts 124 of handgrip 52. As shown, group 126 is located along fingers 114 of glove 108 and group is located on the palm 129 of the glove. Of course, groups 126, 128 may be located elsewhere, such as both along corresponding portions of fingers 114, e.g., group 126 at the tips of the fingers and group 128 at the base of the fingers, or each on different fingers, among other locations. In addition, each group 126, 128 may be replaced with a sole contact for completing the corresponding side of the circuit. Contacts 122 may be in electrical communication with the respective positive and negative sides of batteries 104', e.g., via individual wires (not shown) or metal fabric, netting, foil, or other structure sewn into, or otherwise provided to, glove 108. Those skilled in the art will readily understand how contacts 122 may be formed, attached to glove 108, and placed into electrical communication with batteries 104' so that a detailed explanation need not be provided herein.

Each electrical contact 124 of handgrip 52 may be a metal plate conforming to the desired shape of gripping surface 130 of handgrip. In the embodiment shown, two such contacts 124 are provided, one for the positive side of the circuit and one for the negative side of the circuit. Each contact 124 may extend the entire length of handgrip 52 and be electrically insulated from the other contact by an insulating material, e.g., plastic or wood, among others, that may form the rest of the handgrip or a portion thereof. Alternatively, electrical contacts 124 may extend only along a portion of the length of handgrip 52, e.g., a central portion, corresponding to a region that user 27 would more likely than not grip during any given exercise performed with exercise device 20. Moreover, depending upon the configuration of electrical contacts 122 of glove 108, handgrip 52 may be provided with two or more electrical contacts 124 for each of the positive and negative sides of the circuit. If monitor 94 and/or electronic display 88 are in a location remote from force measuring system 28, electrical power may be provided thereto via wires (not shown) electrically connected to contacts 124 of handgrip 52. Those skilled in the art will understand the many arrangements of contacts 122 of glove 108 and contacts 124 of handgrip 52 that are possible such that an exhaustive recitation in not required herein.

Alternatively, and as illustrated in FIG. 4, glove 108 may optionally include an electronic display 88' in addition to, or in lieu of, an electronic display provided elsewhere, e.g., on monitor 94 or housing 82 of force measuring system 28. Electronic display 88' may be powered by batteries 104' aboard glove 108 and may receive the applied force signal from force measuring system 28 via a receiver (not shown) similar to receiver described above in connection with monitor 94. In addition, if force measuring system 28 is provided with other features, e.g., the force storage and retrieval and repetition counting features discussed above, having controls onboard glove 108, a transceiver (not shown) may be used in lieu of the receiver. Moreover, the applied force signal may be communicated to electronic display 88' via electrical contacts 122, 124 of glove 108 and handgrip 52 or other contacts (not shown) on the glove and handgrip. In lieu of contacts 122, 124 of glove 108 and handgrip 52, electrical power may be communicated to force measuring system 28, monitor 94, and/or electronic display 88 via a suitable cable (not shown), or other electrical conductor, that may, e.g., be removably connectable with one or both of battery compartment 120 and force measuring system 28.

Figure 7:
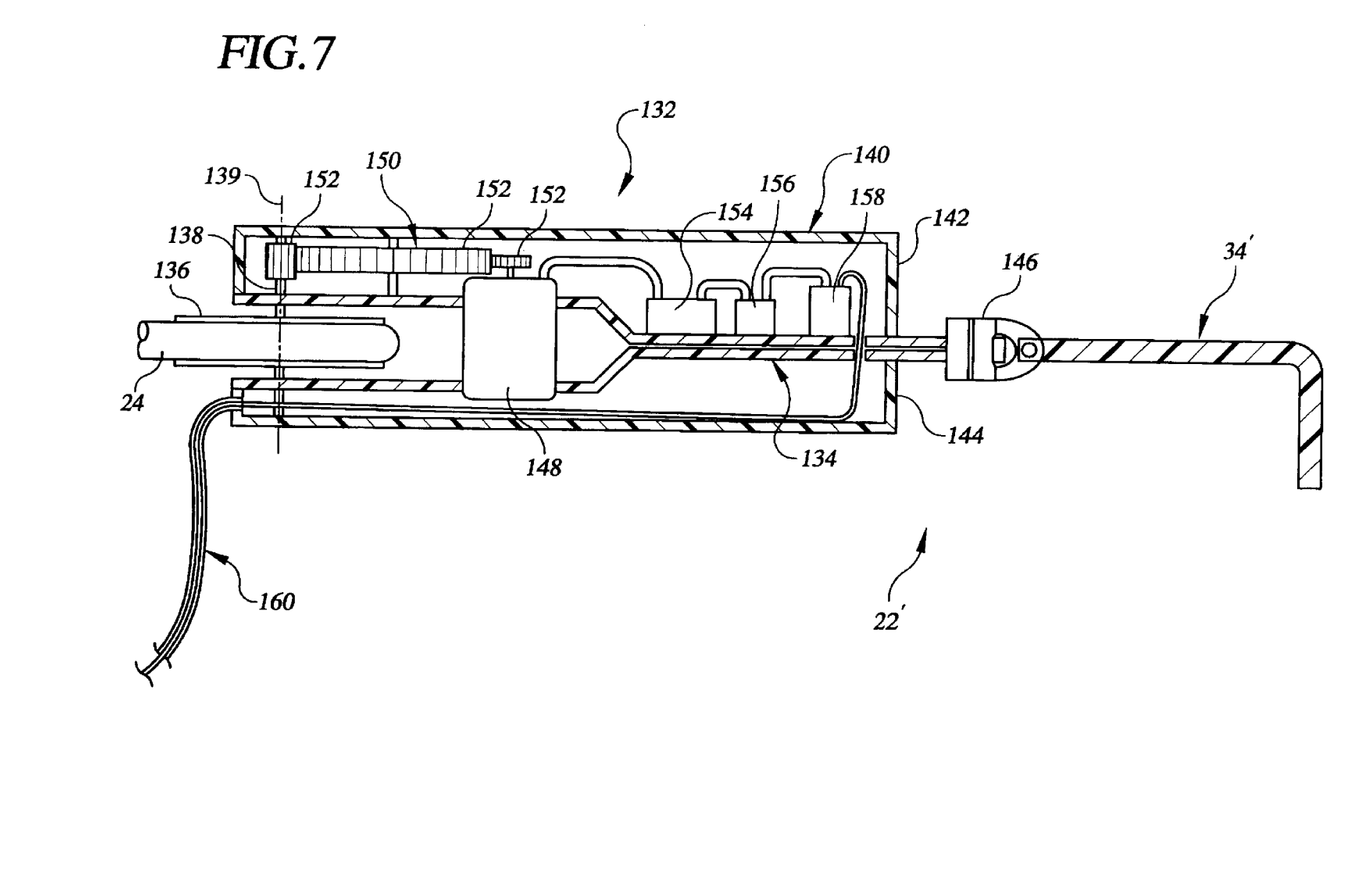
FIG. 7 is an elevational cross-sectional view and simplified schematic diagram of an alternative pulley/securing device assembly having a generator for generating power for various electronic devices that may be part of an exercise device of the present invention.

Referring to FIG. 7 and also to FIG. 1, in yet another embodiment, electrical power may be provided to force measuring system 28, monitor 94, and/or electronic display 88 from a power generating system 132 that may be incorporated into pulley/securing device assembly 22'. Like pulley/securing device assembly 22 of FIGS. 1 and 2, assembly 22' may include a securing device 34' configured for securing exercise device 20 to a stationary object, such as door 46 of FIG. 1. For example, securing device 34' may be configured to be hooked over the top of a swing-type door and captured in the space between door 46 and upper portion of the doorjamb 48, as shown in FIG. 1. Of course, securing device 34' may be any other type of device for securing exercise device 20 to objects other than doors. Those skilled in the art will be familiar with the various securing devices 34' that may be provided such that an exhaustive recitation need not be presented herein.

Assembly 22' may include a block 134 and a pulley 136, which may include a central shaft 138 affixed thereto. As user alternatingly moves gripping structures 26 back and forth in a reciprocating manner, cord 24 drives pulley 136 in alternating directions about the longitudinal axis 139 of central shaft 138. Assembly 22' may also include a housing 140 comprising one or more components, such as upper housing member 142 and lower housing member 144, that enclose the various mechanical and electrical components of power generating system 132. Central shaft 138 of pulley 136 may be supported by block 134 and/or housing 140 by any means (not shown) know in the art, such as bearings. Block 134 may be connected to securing device 34' with any suitable means, such as the pivot and swivel connector 146 shown.

Power generating system 132 may include a generator 148 for generating the electrical power needed to energize force measuring system 28, monitor 94, and/or electronic display 88. Generator 148 may be engaged with, and supported by, block 134 and/or housing 140. Suitable generators for power generating system 132 of the present invention are commercially available from a number of sources. Generator 148 may be mechanically coupled to pulley 136 in any know manner, so that the pulley drives the generator when user pulls on cord 24 during use. For example, generator 148 may be coupled to central shaft 138 of pulley 136 by a transmission 150 containing two or more cogged gears 152, such as the three-gear transmission shown. Alternatively, generator 148 may be directly driven, e.g., directly by central shaft 138, or indirectly through various transmissions other than the geared transmission 150, such as a belt and pulley assembly, a driven shaft assembly, or a worm-gear assembly, among others. Those skilled in the art will understand the variety of mechanical couplings that may be made between pulley 136 and generator 148 so that the pulley may drive the generator. In the present embodiment, transmission 150 is geared so that generator 148 is driven in the same direction as pulley 136. However, in alternative embodiments, transmission 150 may be configured so that generator 148 is driven in a direction opposite from pulley 136 or in only one direction, regardless of the direction the pulley is driven by user 27. Those skilled in the art will readily understand the variety of transmissions 150 that may be used with power generating system 132 of the present invention, such that each need not be described in detail.

When generator 148 is driven by pulley 136 in an alternating fashion by user 27 moving gripping structures 26 in a reciprocating manner, the electrical current output from the generator will be an alternating current (AC). Accordingly, power generating system 132 may also include a rectifier 154 in electrical communication with generator 148 for rectifying this AC electricity into DC electricity. Power generating system 132 may also include additional signal conditioning circuitry 156 for further conditioning the electrical signal from generator 148 for use by force measuring system 28, monitor 94, and/or electronic display 88. Power generating system 132 may optionally include a battery 158, or other storage device, for storing electrical energy from generator 148, e.g., for energizing force measuring system 28, monitor 94, and/or electronic display 88 when user is not driving pulley 136 and/or when the power generated by the generator is otherwise insufficient to fully energize the force measuring system, monitor, and/or electronic display. Battery 158 may be in electrical communication with force measuring system 28, monitor 94, and/or electronic display 88 via one or more power cables 160 or other electrical conductors. Those skilled in the art will readily understand the generally simple electronics involved with implementing power generating system 132 of the present invention.

Referring again to FIG. 3, in an alternative embodiment of exercise device utilizing a piezoelectric sensor 72, the power needed to energize force measuring system 28 and monitor 94 may be generated by the piezoelectric sensor. This provides a non-mechanical, on-board energy source that does not include the shortcomings normally attendant mechanical system, such as mechanical wear and relative inefficiency, among others, and does not require the replacement of batteries. As user 27 (FIG. 1) applies force 68 to handgrips 52 during an exercise, a voltage is induced across piezoelectric sensor 72. Thus, piezoelectric sensor 72 may be electrically connected to a rectifier, storage battery, and/or conditioning circuitry similar to such items described in connection with power generating system 132 of FIG. 7, and/or other electronics/devices, for providing the power necessary to energize the various systems of force measuring system 28 and monitor 94. Those skilled in the art will understand not only the various components that may be used for utilizing piezoelectric sensor 72 as a power source, but also how to interconnect these components to make a properly functioning system. Therefore, a detailed description of such a system need not be presented herein.

Figure 8:
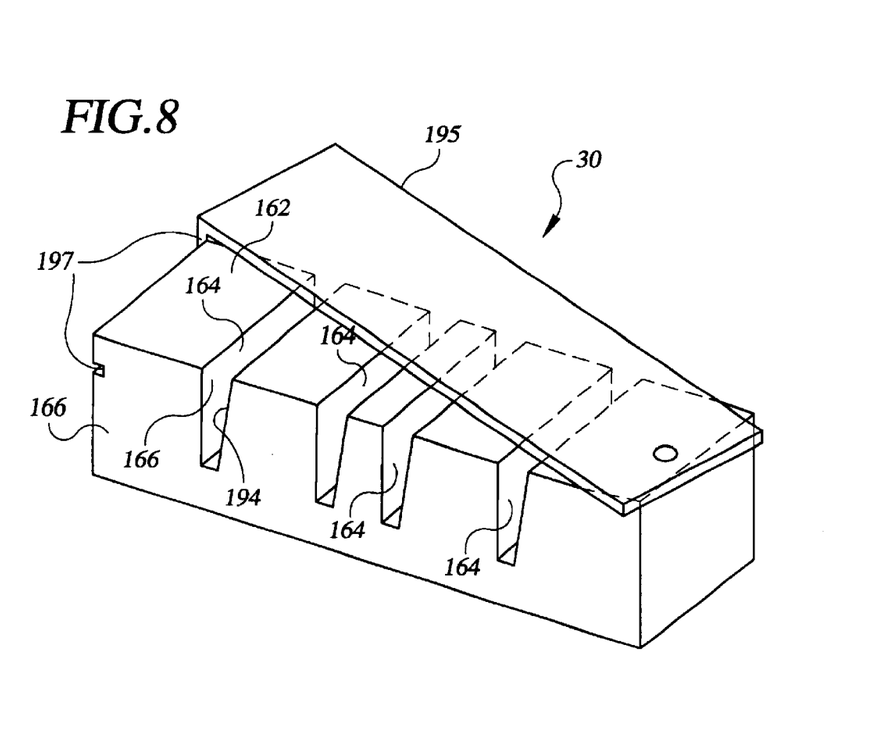
FIG. 8 is a perspective view of the length adjuster of the exercise device of FIGS. 1 and 2.
Figure 9:
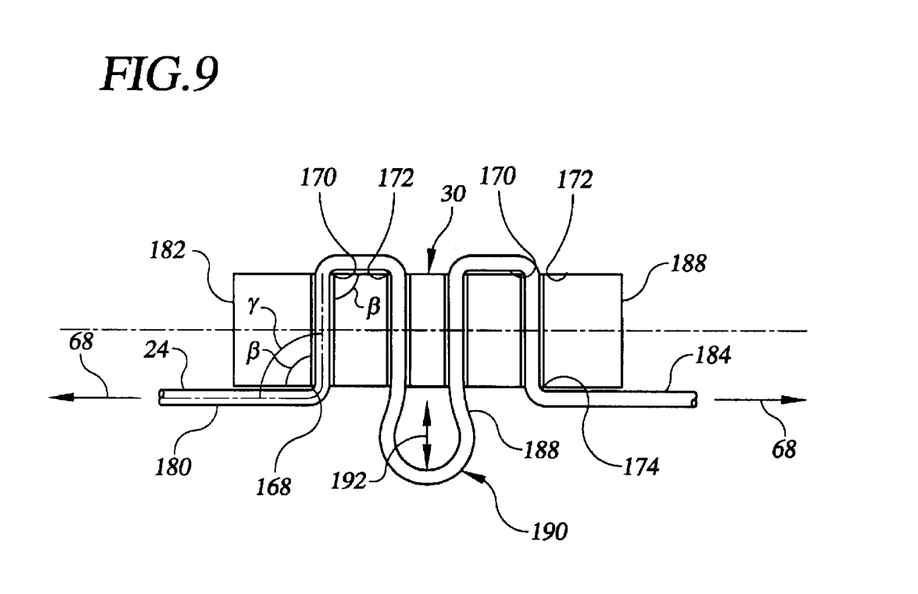
FIG. 9 is a plan view of the cord length adjuster of FIG. 8 without the cover showing a cord threadedly engaged therewith.

Referring now to FIGS. 8 and 9, length adjuster 30 may comprise a body 162 having a plurality of slots 164 formed therein for receiving cord 24 and allowing the cord to be threadedly engaged with the body in a circuitous manner among the plurality of slots. An important feature of length adjuster 30 is that it allows user 27 (FIG. 1) or other person to readily adjust the length of cord 24 without having to cut the cord. Rather, the arrangement and configuration of slots 164 allow length adjuster to be conveniently installed onto cord 24 generally from the side of the cord. Slots 164 are arranged with respect to one another and/or sides 166 of body 162 so that the slots form a plurality of outside corners, e.g., corners 168, 170, 172, and corners 174, 176, 178, that each form an angle β and may aid in transferring tensile force 68 in a portion 180 of cord 24 adjacent one end 182 of body 162 into the body and transferring the tensile force in the body to a portion 184 of the cord adjacent the opposing end 186 of the body so that an intermediate portion 188 of the cord is generally-slack, i.e., does not contain tensile force 68 or portion thereof. Accordingly, user 27 (FIG. 1) may adjust the effective length of cord 24, i.e., the maximum distance between gripping structures 26 (FIGS. 1 and 2), by forming an excess loop 190 from intermediate portion 188 of the cord and adjusting the size of the excess loop as illustrated by bi-directional arrow 192.

In general, angle β may be any angle desired, but an angle of 90° or less is preferred because of the greater interaction that may occur between cord 24 and outside corners 168, 170, 172 at such angles. Outside corners 168, 170, 172 may be pointed, rounded or otherwise shaped, with pointed being generally preferred, unless the surface of body 162 at the outside corners is roughened, coated, or otherwise prepared to increase the friction between cord 24 and the outside corners.

It is noted that although any number of slots 164 may be used, inventor has found that four slots can be effective in that in one embodiment four slots generally provide three effective outside corners per end 182, 186 of body, e.g., outside corners 168, 170, 172, and outside corners 174, 176, 178, respectively, for transferring tensile force 86 to body 162 and a central location for forming excess loop 190. In addition, in the configuration shown in FIGS. 8 and 9, an even number of slots 164 may be preferable if cord 24 is to be engaged therein as shown, since an even number of slots will result in the cord being on the same side of body 162 at each end 182, 186 thereof, preventing the body from rotating when tensile force 68 is applied. On the other hand, if cord 24 is on opposite sides of length adjuster 30 at opposing ends 182, application of an axial force to the cord will apply a torque to the length adjuster causing it to rotate. Such a rotation, if present, may adversely affect the interaction of cord 24 with outside corners 168–178 due to the angles γ formed between adjacent portions of the cord on either side of the outside corners proximate ends 182, 186 of the body being larger than angle β of the corresponding outside corners as a result of the rotation.

Body 162 may be made of any suitable material, such as plastic, wood, or metal, among others, or combination thereof, and may be any suitable shape desired. The rectilinear embodiment shown in FIGS. 8 and 9 is merely for illustrative purposes only. In general, the width of each slot 164 may be equal to or less than the diameter of cord 24. For example, for a cord 24 having a diameter of one-quarter inch, the width of each slot 164 may be one-quarter inch, or less if the cord is at least somewhat compressible in a direction transverse to its axial direction. Sides 194 of each slot 164 may be parallel to one another, or may be tapered as shown. If sides 194 are tapered, the width of the corresponding slot 164 at its upper end may be equal to or greater than the diameter of cord 24, and the width at the lower end may be less than the diameter of the cord so that user may wedge cord into the slot to provide further interaction between the cord and body to aid in transferring tensile force 68 from the cord to the body at each end of the body. Sides 194 of each slot 164 may also, or alternatively, be knurled or otherwise roughened to increase the interaction between cord 24 and body 162. Among other things, this results in cord 24 being held firmly within slots 164 to reduce the possibility of the cord disengaging one or more of the slots.

In this connection, length adjuster 30 may optionally be provided with a cover 195 for covering the upper surface of body 162 to prevent cord 24 from disengaging the length adjuster via the upper ends of the slots 164. Cover 195 may be pivotably attached to body 162 as shown, or may be removably securable to the body in any suitable manner, such as by snap-fit, sliding engagement with appropriate grooves formed in either the cover or the body, or mechanical fasteners, among others. If cover 195 is pivotably attached to body 162, length adjuster 30 may include a catch mechanism 197, or other means, for securing the cover in a closed position. In an alternative embodiment, a sole cover 195 for covering all slots 164 may be replaced with multiple covers (not shown) that each cover a corresponding slot. Such individual slot covers may slidably engage corresponding grooves in sides 194 of each slot 164, or may otherwise engage body 162. Each slot cover may also include a catch or other means for securing the cover in place.

Figure 10:
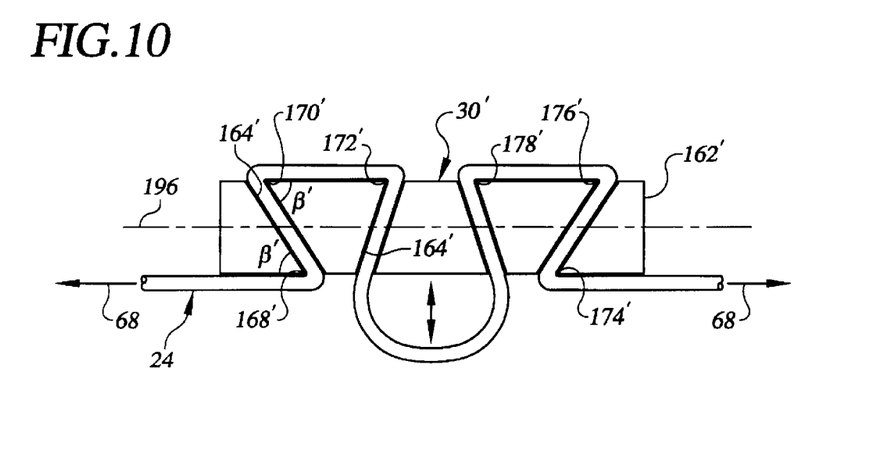
FIG. 10 is a plan view of an alternative embodiment of a cord length adjuster of the present invention.

FIG. 10 shows an alternative embodiment of a length adjuster 30' of the present invention that includes slots 164' that are skewed with respect to the longitudinal axis 196 of body 162'. In addition, immediately adjacent ones of the slots 164' are skewed in opposite directions with respect to one another. When cord 24 is engaged within slots 164' of length adjuster 30' as shown, this configuration of slots provides outside corners 168'–178' that form angles β' smaller than 90°. These smaller angles β' may increase the interaction between cord 24 and each outside corner 168'–178' so that applied force 68 is more effectively transferred to body 162'. Like the embodiment of FIGS. 8 and 9, slots 184' may have parallel or tapered sides and/or may have sides that are knurled or are otherwise roughened to increase the interaction between cord and body.

Figure 11A:
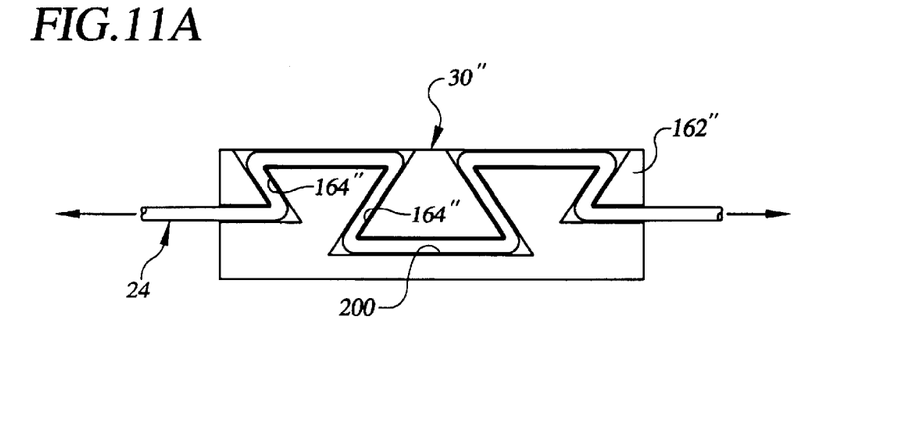
FIGS. 11A and 11B are, respectively, a plan view and an elevational view of another alternative embodiment of a cord length adjuster of the present invention.
Figure 11B:
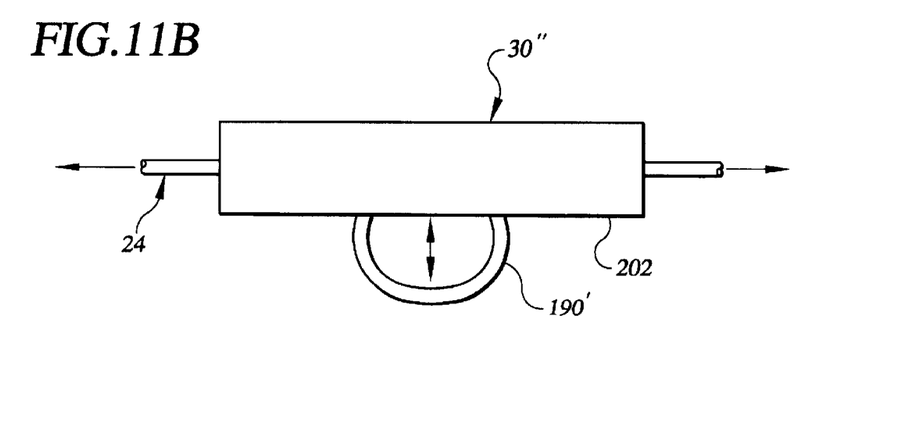

FIGS. 11A and 11B show another alternative embodiment of a length adjuster 30" of the present invention illustrating the diversity of configurations of the length adjuster that is possible. This embodiment shows that slots 164" need not extend from one side of body 162" to another and that excess loop 190' need not be in the same plane as the circuitous configuration that cord 24 takes while engaged with the slots. In this connection, body 162" may include an aperture 200 that allows excess loop 190' to extend through the lower surface 202 of the body. Like the embodiment of FIGS. 8 and 9 and the embodiment of FIG. 10, slots 164" may have parallel or tapered sides and/or may have sides that are knurled or are otherwise roughened to increase the interaction between cord and body.

While the present invention has been described in connection with a preferred embodiment, it will be understood that it is not so limited: On the contrary, it is intended to cover all alternatives, modifications, and equivalents as may be included within the spirit and scope of the invention as defined above and in the claims appended hereto.

What is claimed is:

1. A system, comprising:
   a) an exercise device that provides a resistive force to a user; and
   b) a force measuring system for measuring said resistive force, said force measuring system including:
      i) a generally trangular-shaped force-carrying element comprising:
         A) a first leg and a second leg that generally converge with one another to form a crotch having a center, each of said first and second legs having a distal end spaced from said crotch; and
         B) a third leg extending between said distal ends of said first and second legs to keep said distal ends spaced from one another: and
      ii) a sensor, operatively coupled to said first and second legs between said crotch and said third leg, for sensing a change in distance between said first and second legs when said resistive force is applied to said third leg along a line extending through said center of said crotch.

2. A system for measuring a force, comprising:
   a) a generally triangular-shaped force-carrying element comprising:
      i) a first leg and a second leg that generally converge with one another to form a crotch having a center, each of said first and second legs having a distal end spaced from said crotch; and
      ii) a third leg extending between said distal ends of said first and second legs to keep said distal ends spaced from one another, wherein said third leg comprises a handgrip that includes a battery compartment; and
   b) a sensor, operatively coupled to said first and second legs between said crotch and said third leg, for sensing a change in distance between said first and second legs when a force is applied to said third leg along a line extending through said center of said crotch.

3. A system for measuring a force, comprising:
   a) a generally triangular-shaped force-carrying element comprising:
      i) a first leg and a second leg that generally converge with one another to from a crotch having a center, each of said first and second legs having a distal end spaced from said crotch; and
      ii) a third leg extending between said distal ends of said first and second legs to keep said distal ends space d from one another, wherein said third leg comprises a handgrip having a gripping surface that includes electrical contacts; and
   b) a sensor, operatively coupled to said first and second legs between said crotch and said third leg, for sensing a change in distance between said first and second legs when a force is applied to said third leg along a line extending through said center of said crotch.

* * * * *

UNITED STATES PATENT AND TRADEMARK OFFICE
CERTIFICATE OF CORRECTION

PATENT NO. : 6,662,651 B1
DATED : December 16, 2003
INVENTOR(S) : Wilfred Roth It is certified that error appears in the above-identified patent and that said Letters Patent is hereby corrected as shown below:

Column 14,
Line 3, delete "trangular" and insert -- triangular -- therefor.
Line 38, delete "from" and insert -- form -- therefor.
Line 42, delete "space d" and insert -- spaced -- therefor.

Signed and Sealed this

Twenty-second Day of June, 2004

JON W. DUDAS
*Acting Director of the United States Patent and Trademark Office*